(12) United States Patent
Wolfgong et al.

(10) Patent No.: US 10,274,468 B2
(45) Date of Patent: Apr. 30, 2019

(54) METHODS AND KIT FOR DETERMINING PRESENCE OF TRIVALENT CHROMIUM CONVERSION COATING

(71) Applicant: RAYTHEON COMPANY, Waltham, MA (US)

(72) Inventors: William J. Wolfgong, Little Elm, TX (US); Stephen T. Fasolino, McKinney, TX (US)

(73) Assignee: RAYTHEON COMPANY, Waltham, MA (US)

( * ) Notice: Subject to any disclaimer, the term of this patent is extended or adjusted under 35 U.S.C. 154(b) by 46 days.

(21) Appl. No.: 15/353,047

(22) Filed: Nov. 16, 2016

(65) Prior Publication Data
US 2018/0136178 A1    May 17, 2018

(51) Int. Cl.
*G01N 31/22* (2006.01)
*G01N 21/78* (2006.01)
*G01N 31/00* (2006.01)
*G01N 21/75* (2006.01)

(52) U.S. Cl.
CPC .............. *G01N 31/22* (2013.01); *G01N 21/78* (2013.01)

(58) Field of Classification Search
USPC ..................................................... 436/83, 73
See application file for complete search history.

(56) References Cited

U.S. PATENT DOCUMENTS

| 2,902,348 | A | 9/1959 | Ostrander |
| 3,656,908 | A | 4/1972 | Noll et al. |
| 4,546,087 | A | 10/1985 | Wilson |
| 5,165,795 | A | 11/1992 | Hauffe |
| 5,304,257 | A | 4/1994 | Pearlstein et al. |
| 6,375,726 | B1 | 4/2002 | Matzdorf et al. |
| 6,794,651 | B2 | 9/2004 | Shelley et al. |
| 7,148,068 | B1 | 12/2006 | Reheulishvili et al. |
| 7,800,069 | B2 | 9/2010 | Shelley et al. |
| 2010/0032060 | A1* | 2/2010 | Matzdorf ............... C23C 18/08 148/247 |

FOREIGN PATENT DOCUMENTS

WO    9944056 A1    9/1999

OTHER PUBLICATIONS

Gou, Yang, A Study of Trivalent Chrome Process Coatings on Aluminum Alloy 2024-T3, The Ohio State University, 2011, pp. 1-190. (Year: 2011).*

(Continued)

*Primary Examiner* — Christine T Mui
(74) *Attorney, Agent, or Firm* — Lando & Anastasi, LLP

(57) ABSTRACT

A method for testing for the presence of a trivalent chromium conversion coating on a metal substrate is provided. According to one embodiment, the method comprises contacting a surface of the metal substrate with at least one solvent to generate a test solution, adding an indicator capable of detecting zirconium to the test solution in an amount sufficient to induce a color change of the test solution if zirconium is present in the test solution, and determining whether a color change indicating the presence of the conversion coating occurs in the test solution.

19 Claims, 6 Drawing Sheets

(56) References Cited

OTHER PUBLICATIONS

Kennedy, David Colin, Sulfoxides as solvent extraction reagents for the analytical separation of metal ions, (1969). Retrospective Theses and Dissertations. 3583. (Year: 1969).*
Staff, Ames Laboratory and Spedding, F. H., Semi-annual summary research report in chemistry (1957). Ames Laboratory ISC Technical Reports.161. (Year: 1957).*
Qi, J.T., et al, Trivalent chromium conversion coating formation on aluminum, Surface & Coatings Technology, 2015, 280, 317-329. (Year: 2015).*
Hummers et al. "Zirconium and Hafnium Tetrachlorides" Inorganic Syntheses, vol. IV, 1953, pp. 121-126.

\* cited by examiner

METHODS AND KIT FOR DETERMINING PRESENCE OF TRIVALENT CHROMIUM CONVERSION COATING

BACKGROUND

Chromate conversion coatings are often used to protect metal surfaces such as aluminum, zinc, steel, cadmium, copper, silver, magnesium, tin, and alloys of these metals, from corrosion. After treatment, the resulting coating becomes an integral part of the metal surface and provides corrosion resistance as well as an inert surface that can be used for further processing, such as painting or other finishes, including electroplating.

Chromate conversion processes have historically used a chemistry based on hexavalent chromium. However, hexavalent chromium ($Cr^{VI}$ or Cr(VI)) is prohibited and banned in many regions of the world due to its toxicity and the hazards it poses to human health and the environment. For instance, hexavalent chromium has been shown to be a human respiratory carcinogen. Trivalent chromium ($Cr^{III}$ or Cr(III)) has shown in certain instances to be as effective as hexavalent chromium in providing protection against corrosion, and is much less harmful to the environment and human health.

Trivalent chromium conversion processes typically include using trivalent chromium ($Cr^{+3}$) and chemicals such as deoxidizers and/or acids that dissolve the surface of the metal to form a film that functions as the conversion coating. For instance, one example of a trivalent chromium conversion process for aluminum and aluminum alloy metal substrates is performed at ambient temperatures and includes an acidic aqueous coating bath that contains an alkali metal hexafluorozirconate ($ZrF_6^{-2}$), a water-soluble trivalent chromium salt ($Cr^{+3}$), and sulfate ($SO_4^{-2}$) (for acidity). The conversion coating is formed by a reaction between ions in the bath and metal cations of the base metal that is dispersed in the bath. The United States Navy has developed standards for trivalent chromium conversion on aluminum substrates, including MIL-DTL-5541 and MIL-DTL-81706B.

Despite the absence of hexavalent chromium in the trivalent chromium conversion process, in certain instances hexavalent chromium species in coatings have been found to exist and are thought to result from oxidation of trivalent chromium. In some instances, hexavalent chromium processes result in conversion to trivalent chromium. Because of the detrimental effects on human and environmental health related to hexavalent chromium, accurate speciation information is important in analyzing a treated metal surface.

SUMMARY

Aspects and embodiments are directed to methods that test for the presence of a conversion coating on metal substrates that have been subjected to a trivalent chromium conversion process.

According to one embodiment, a method of testing for the presence of a conversion coating on a metal substrate that has been subjected to a trivalent chromium conversion process comprises contacting a surface of the metal substrate with at least one solvent to generate a test solution, adding an indicator capable of detecting zirconium to the test solution in an amount sufficient to induce a color change of the test solution if zirconium is present in the test solution, and determining whether a color change indicating the presence of the conversion coating occurs in the test solution.

According to one embodiment, a method for testing the presence of a conversion coating on a metal substrate that has been subjected to a trivalent chromium conversion process comprises obtaining a sample of the metal substrate, contacting a surface of the sample of the metal substrate with at least one solvent to generate a test solution, adding an indicator capable of detecting zirconium to the test solution in an amount sufficient to induce a color change of the test solution if zirconium is present in the test solution, and visually observing whether a color change result occurs within the test solution containing the indicator thereby indicating the existence or the absence of the conversion coating.

According to one embodiment, a method for detecting the presence of a trivalent chromium conversion coating on a surface of a metal substrate that has been subjected to a trivalent chromium conversion process comprises contacting a surface of the metal substrate with at least one solvent to generate a test solution, adding an indicator capable of detecting zirconium to the test solution in an amount sufficient to induce a color change of the test solution if zirconium is present in the test solution, determining whether a color change indicating the presence of the conversion coating occurs in the test solution, and using the metal substrate in at least one of a decorative and functional application if the determination of the presence of the conversion coating is confirmed.

In one example the at least one solvent is capable of dissolving zirconium. In another example the at least one solvent comprises at least one protic acid. In another example the at least one protic acid is one of hydrochloric acid, hydrofluoric acid, and nitric acid.

According to one example, contacting the surface of the metal substrate comprises contacting the surface of the metal substrate with at least one base, and contacting the surface of the metal substrate with at least one acid. In one example the at least one base is a basic solution.

In another example the method further comprises contacting the surface of the metal substrate with a flux material, and heating the metal substrate to a predetermined temperature prior to contacting the surface of the metal substrate with the at least one solvent. In one example the flux material is a solid basic salt. In one example the solid basic salt is a borate or a carbonate of an alkali metal. In another example, the at least one solvent is a protic acid. In another example, the at least one solvent includes at least one additive. In one example the at least one additive is one of an oxidizing agent and a reducing agent.

In one example the indicator does not chemically react with any alloys present in the metal substrate. In one example the indicator is one of morn hydrate and arsenazo I hydrate.

According to another embodiment a kit for determining the presence of a conversion coating on a metal substrate that has been subjected to a trivalent chromium conversion process comprises a solvent and an indicator capable of detecting zirconium in a test solution formed from contacting the solvent with a surface of the metal substrate.

In one example, the indicator induces a color change of the test solution if zirconium is present in the test solution. In another example, the solvent is capable of dissolving zirconium. In one example the solvent comprises at least one protic acid. In one example the at least one protic acid is one of hydrochloric acid, hydrofluoric acid, and nitric acid.

According to one example, the kit further comprises a flux material. In one example, the flux material is a borate or a carbonate of an alkali metal. In one example, the indicator is one of morn hydrate and arsenazo I hydrate. In one example, the solvent and the indicator are provided together in a single solution.

In one example, the kit further comprises at least one dispensing device for dispensing at least one of the solvent and the indicator onto the surface of the metal substrate.

Still other aspects, embodiments, and advantages of these example aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Embodiments disclosed herein may be combined with other embodiments, and references to "an embodiment," "an example," "some embodiments," "some examples," "an alternate embodiment," "various embodiments," "one embodiment," "at least one embodiment," "this and other embodiments," "certain embodiments," or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

DETAILED DESCRIPTION

Figure 1:
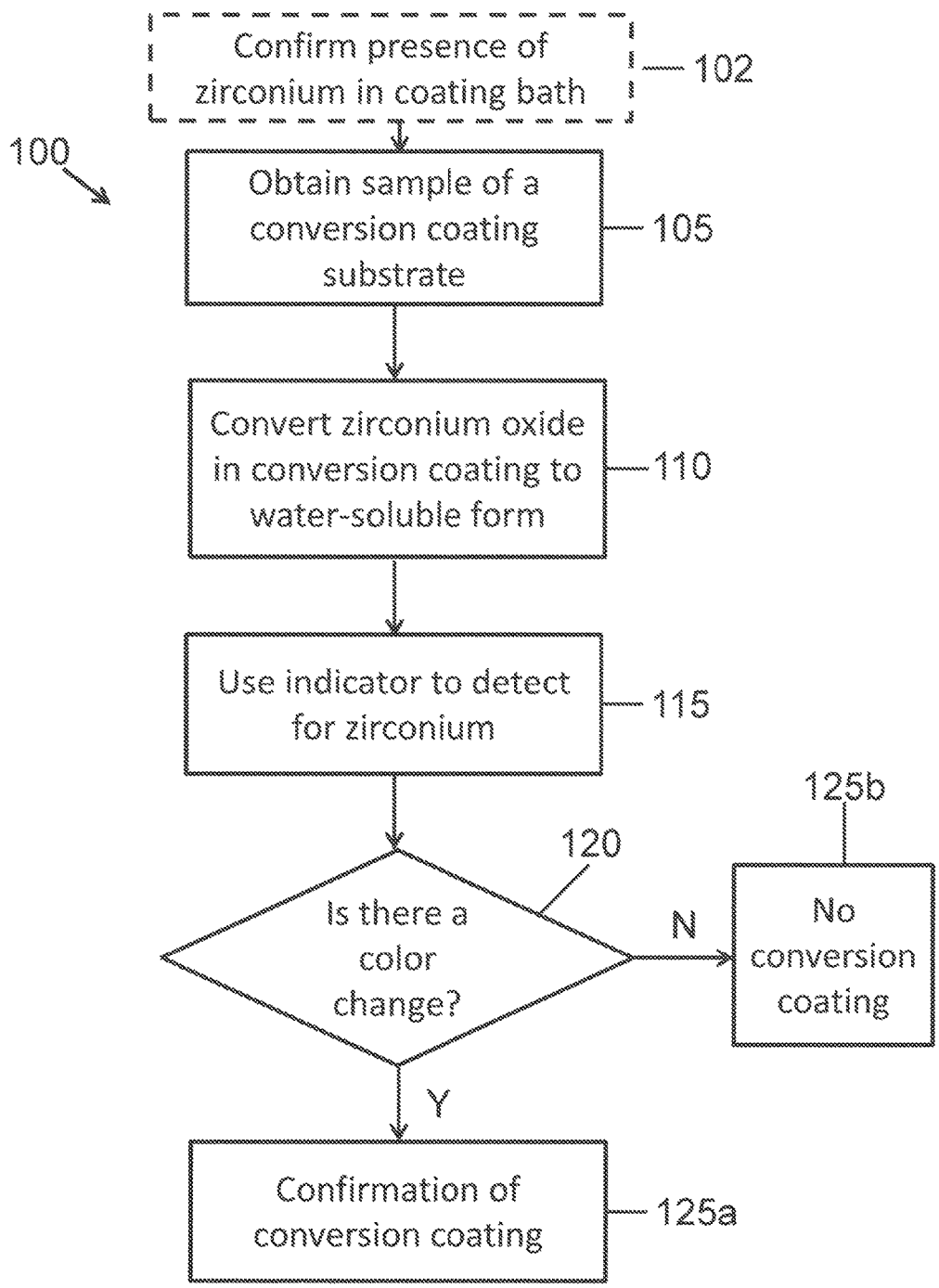
FIG. 1 is a functional block diagram illustrating one example of a testing process flow according to aspects of the present invention.

Confirming the presence of trivalent chromium in a conversion coating on a metal substrate can be difficult in that new conversion coatings may be transparent and it is therefore difficult to determine whether the coating is present on a metal surface based on the coating's color. Typical testing methods for confirming the presence of the coating and the formation of trivalent chromium include scanning electron microscope (SEM) analysis, spectrometry, and spectrophotometric techniques. These methods, however, are expensive, require complex instrumentation and small treated metal sample sizes, and are generally inaccessible to most metal shops that perform the conversion process.

Besides the methods discussed above, colorimetric analysis techniques may also be used for determining the presence of a chromate conversion coating. These methods include spot testing the metal using a chemical solution that dissolves the coating. A color reagent then reacts with the chromium in the solution and causes a color change that indicates the presence of chromium, and hence, the presence of the conversion coating. However, many alloys that form metal substrates, including aluminum and nickel alloys, contain chromium, which creates a false positive when this type of colorimetric test is performed.

Many trivalent chromium conversion processes, including the trivalent conversion process discussed above, use zirconium, and the conversion coatings that result from these processes contain high levels of zirconium compounds, i.e., greater than 10-20%. In these processes, the zirconium is deposited in the mixed metal oxide that comprises the conversion coating, and therefore the conversion coating comprises zirconium oxide. In contrast, hexavalent chromium coating products, including hexavalent conversion coatings, contain either no zirconium or very low levels of zirconium, i.e., less than 1%. Furthermore, unlike chromium, zirconium is not a typical component of alloys that may form the metal substrate, including aluminum alloys, which reduces the likelihood of obtaining a false positive result. Aspects of this disclosure take advantage of the higher levels of zirconium in the trivalent chromium conversion coating and the fact that zirconium is not a typical component of metal alloys, and embodiments are directed to various methods that include zirconium in verifying the presence of a trivalent chromium conversion coating. Embodiments of this disclosure include testing methods for the presence of trivalent chromium conversion coatings that may not require expensive equipment, may be performed on large samples, may be performed on metal alloy substrates that contain chromium, and may give quick and reliable results.

In accordance with various embodiments, at least one colorimetric test is provided that is capable of determining the presence of a trivalent chromium conversion coating. Discussed below are several different types of tests that use colorimetric analysis to determine the presence of a trivalent chromium conversion coating on a metal substrate. The metal substrate may be any metal substrate that has undergone a chromate conversion coating process. Non-limiting examples of metal substrates include aluminum, zinc, cadmium, copper, silver, magnesium, tin, and alloys of any one of these metals, and steel. The methods disclosed herein may be used on conversion coatings having a thickness in a range of approximately 0.25 to 1 micron, although it is within the scope of this disclosure for the methods to be applied to coatings that are thicker, i.e., greater than 1 micron, or thinner, i.e., less than 0.25 microns.

Example Testing Process Flow

An overview of the methods disclosed herein is shown in FIG. 1. Specifically, FIG. 1 is a functional block diagram that shows one example of a testing process flow according to various aspects of the methods discussed below. The process flow, generally indicated at 100, begins at step 105 with obtaining a sample of a conversion coating substrate. The substrate may be a metal substrate, as described above. For instance, the metal substrate may be any metal substrate that has undergone a chromate conversion coating process, including aluminum, aluminum alloy, magnesium, tin, and steel substrates. As discussed above, the conversion coating process typically includes zirconium in the conversion bath. In certain instances, a determination step may also be included in the process for verifying that zirconium was included in the coating bath that formed the conversion coating on the metal substrate. This is shown in the flow diagram as step 102.

Once a sample of the metal substrate has been obtained, any zirconium oxide present in the conversion coating may be converted to a water-soluble form in step 110. This may be accomplished using any of the methods discussed below. For instance, the process may comprise contacting a surface of the metal substrate with at least one solvent to generate a test solution. The solvent may be capable of dissolving zirconium and therefore may be capable of reacting with zirconium oxide present in the coating to form a water-soluble form of zirconium, such as a zirconium salt or complex. In some embodiments, the solvent comprises one or more protic acids. For instance, according to one embodiment, hydrochloric acid may be used as the solvent to generate zirconyl chloride, which is a water-soluble form of zirconium. According to another embodiment, nitric acid may be used to generate zirconyl nitrate, which is another example of a water-soluble form of zirconium. According to yet another embodiment, hydrofluoric acid may combine with zirconium to generate a water-soluble form of zirconium. According to some embodiments, the process may comprise contacting the surface of the metal substrate with one or more bases, such as a basic solution, prior to contacting the surface of metal substrate with one or more acids. For instance, in one embodiment, the surface of the metal substrate may first be contacted with potassium hydroxide, and then the surface may be contacted with hydrochloric acid to generate a water-soluble form of zirconium.

According to other embodiments, converting the zirconium oxide present in the conversion coating to a water-soluble form in act 110 may further comprise contacting the surface of the metal substrate with a flux material, such as a solid basic salt, and then heating the substrate, as described in further detail below. For instance, a solid basic salt such as a borate and/or a carbonate of an alkali metal may first be deposited onto the surface of the metal substrate and then heated to a temperature of about 1000° C. After heating, the process may include adding a solvent, such as a protic acid, e.g., hydrochloric, hydrofluoric, or nitric acid, to generate a water-soluble form of zirconium.

In accordance with another embodiment, hydrolysis may be used to convert zirconium present in the conversion coating into a water-soluble form, as described below.

In step 115, an indicator may be used to detect for zirconium. For instance, one of morin hydrate or arsenazo I hydrate may be added to a test solution comprising the solvent and any dissolved zirconium, e.g., a test solution formed from a protic acid (aqueous) and the water-soluble form of zirconium. As discussed in more detail below, the indicator changes color in the presence of zirconium, and at step 120 a determination is made as to whether a color change has occurred. In some embodiments, step 120 may include visually observing whether a color change result occurs within the test solution containing the indicator thereby indicating the existence or the absence of the conversion coating. As discussed herein, in some embodiments, the color change can be determined by the naked eye, and in other instances a device may be used to detect the color change. If the determination at step 120 is yes, then the presence of a trivalent chromium conversion coating is confirmed (step 125a). If the determination at step 120 is no, then there is no confirmation of the formation of a trivalent chromium conversion coating on the surface of the metal substrate (step 125b).

Process 100 depicts one particular sequence of acts in a particular embodiment. Some acts, such as step 102, are optional and, as such, may be omitted in accordance with one or more embodiments. Additionally, other acts can be added, without departing from the scope of the embodiments described herein. For instance, the process may further include using the metal substrate in an application if the presence of the conversion coating is confirmed. For example, the metal substrate may be used in at least one of a decorative and functional application. Non-limiting examples of functional applications include using the metal substrate to provide corrosion resistance, as a base or bonding surface for paint, and in a chemical polishing application. One non-limiting example of a decorative application is to use the metal substrate in a metal coloring application. The metal substrate may be used in a number of different applications, e.g., for aircraft and aerospace structural components, construction applications, mechanical applications, including heat exchanger parts, and containers, including beverage cans.

Method 1—Colorimetric Test with Liquid Solvent

Figure 2:
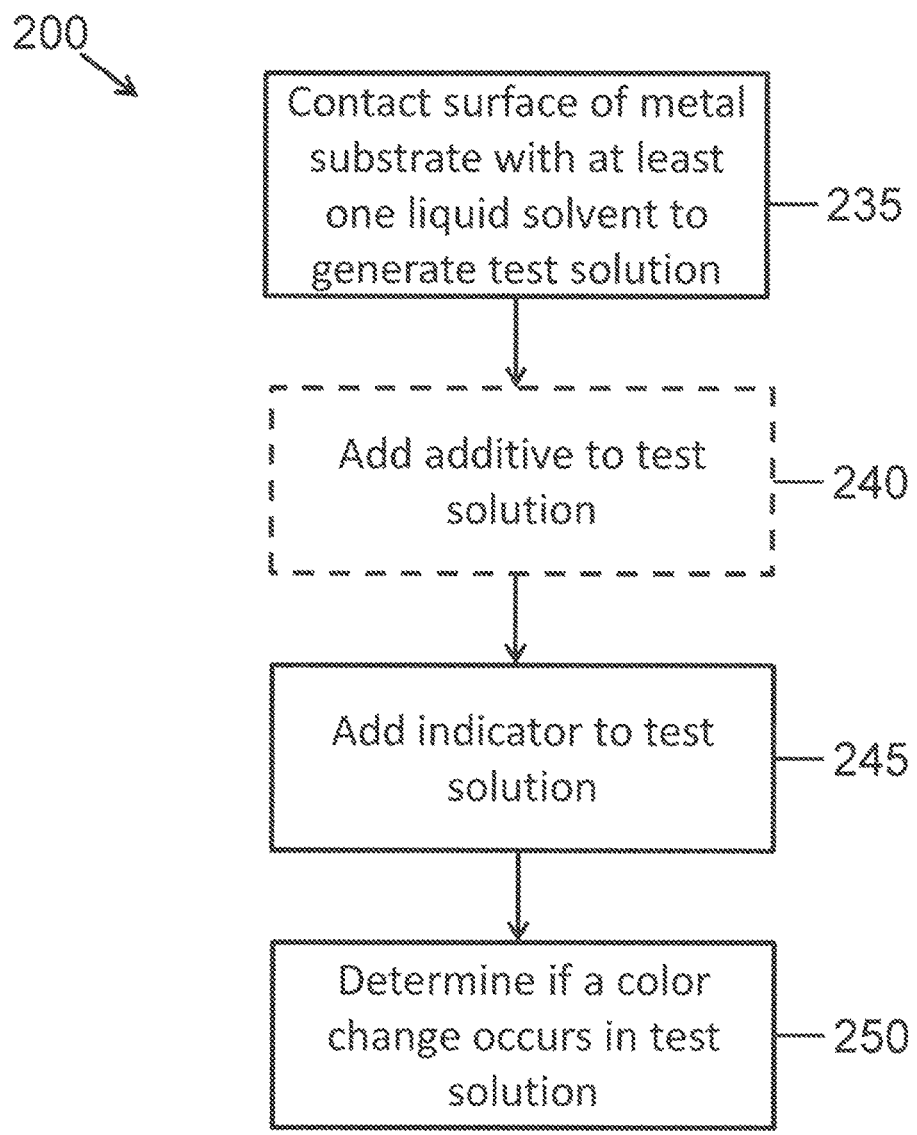
FIG. 2 is a functional block diagram illustrating one example of a colorimetric test method using liquid solvent in accordance with one or more aspects of the present invention.

According to one embodiment, a colorimetric test using one or more liquid solvents is used to confirm the presence of a trivalent chromium conversion coating on a metal substrate, and is generally indicated at 200 in the process flow diagram shown in FIG. 2. The method 200 may include contacting a surface of the metal substrate with at least one solvent to generate a test solution (step 235). In some embodiments, the solvent is capable of dissolving zirconium. The solvent may be any one or more of a number of different solvents, including acids or bases. As used herein, the term "solvent" refers to a substance that may be used alone or in combination with another substance for the purposes of converting or otherwise rendering zirconium into a water-soluble form such that it can be detected.

In some embodiments, contacting the surface of the metal substrate with the solvent may comprise adding one or more drops of solvent to the metal substrate. This type of contact may be suitable for substrates that are large in size. In other embodiments, the metal substrate may be partially or fully immersed in the solvent. The solvent may be dispensed as liquid drops from a dropper, such as an eye dropper, or other dispensing device, such as a syringe or pipette. For instance, according to some embodiments, a pipette may dispense a large single drop of solvent onto the surface of the metal substrate. The drop size may vary in accordance with the composition of the solvent and the size of the pipette. For instance, a 3 mL sized pipette may be suitable for the processes disclosed herein. Suitable pipettes are readily available on the market, such as the Sterilin™ line of transfer pipettes available from Thermo Fisher Scientific (Waltham, Mass.).

According to some embodiments, the solvent comprises one or more acids. In certain embodiments, the solvent comprises one or more protic acids. The term "protic acid" refers to any acid capable of providing an ionizable hydrogen, i.e., a proton. Non-limiting examples of protic acids include hydrochloric, nitric, sulfuric, perchloric, acetic, phosphoric, polyphosphoric, carboxylic, hydrobromic, and hydrofluoric, and any combination thereof. For example, according to one embodiment, the solvent comprises a mixture of hydrochloric and perchloric acids. The acid or acid mixtures allow for the conversion of zirconium present in the coating to be converted to a water-soluble form, i.e., a water-soluble zirconium salt or water-soluble zirconium complex, as generally described by the reaction shown in Equation (1) below:

Equation (1):

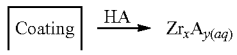

where: HA is a protic acid with H being the proton of the protic acid, A is the anion of the protic acid, and x and y are dependent on the applied acid. For instance, Equation (1a) below reflects the reaction of zirconium oxide and hydrochloric acid to form zirconyl chloride (also referred to as zirconium oxychloride), which is a water-soluble form of zirconium:

$$ZrO_2 + 2HCl + 7H_2O \rightarrow ZrOCl_2 \cdot 8H_2O \text{ (or } [Zr_4(OH)_8(H_2O)_{16}]Cl_8(H_2O)_{12})$$ Equation (1a):

The acid may be of any concentration capable of rendering zirconium into a soluble form for the purposes of performing the testing methods discussed herein.

In accordance with some embodiments, the solvent may comprise one or more bases. As discussed further below, the base may be a basic salt and may be added in the form of a solid or in the form of an aqueous solution.

According to one embodiment, the one or more bases comprise one or more basic solutions, such as an aqueous basic solution. Non-limiting examples of basic solutions include hydroxide solutions such as potassium hydroxide and sodium hydroxide. In some instances, calcium hydroxide and magnesium hydroxide solutions may be used. Other non-limiting examples of basic solutions include bicarbonates and carbonates, such as sodium carbonate and potassium carbonate.

The concentration of basic solution may depend on the type of basic solution used. In some embodiments, the basic solution may be at a concentration of 50 wt % or higher. In some embodiments, the basic solution may be dilute, i.e., a concentration of less than 1 wt %. According to some embodiments, the basic solution may be a 50% by weight aqueous hydroxide solution. Treatment of the metal substrate with the basic solution converts zirconium present in the metal substrate to a zirconium salt as shown in the first part of the reaction described by Equation (2) below. The basic solution may be any concentration capable of converting zirconium in the coating to a zirconium salt for the purposes of performing the testing methods discussed herein. In some instances, the zirconium salt formed from treatment with the basic solution is a water-insoluble zirconium salt. Upon treatment with acid, as discussed below, the zirconium is rendered into a water-soluble form.

In accordance with some embodiments, the zirconium salts formed from treatment with the basic solution may subsequently be treated with one or more acids to convert the zirconium salts to a water-soluble form, i.e., a water-soluble zirconium salt, as shown in the second part of the reaction described by Equation (2) below:

Equation (2):

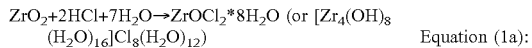

where: C is a cation of a base salt, B is a basic anion of a base salt, H is the proton of a protic acid, A is the anion of the protic acid, and x and y are dependent on the applied base and acid. The one or more acids may be the same acids as discussed above in reference to Equation (1). According to one example, the metal substrate may be sequentially treated with a basic solution for purposes of releasing the oxide coating from the substrate to make the coating more amenable to the acidic conversion of the zirconium oxide to a soluble form (as outlined above in Equation (1a)). Therefore, act 235 of FIG. 2 may comprise a sequential treatment using a liquid base solvent first, and then a liquid acidic solvent.

In some embodiments, the solvent may also include one or more additives. The use of the additive is optional, and may be added to the test solution after contacting the surface of the metal, as shown in step 240 of FIG. 2, or may be added to the liquid solvent before contacting the surface of the metal substrate. For instance, one or more additives may be mixed with solvent prior to contacting the metal substrate.

According to one embodiment, the additive may be an oxidizing agent. Non-limiting examples of oxidizing agents include hydrogen peroxide, nitrogen oxide (fuming nitric acids), chromate salts, sulfur oxides (fuming sulfuric acids), oxalic acid, and persulfate salts. In accordance with at least one embodiment, the solvent comprises one or more acids and an additive that is an oxidizing agent. Oxidizing agents typically refer to substances capable of oxidizing. In certain instances, adding one or more oxidizing agents to an acidic solvent may enhance the effectiveness of the resulting solution. According to another embodiment, the additive may be a reducing agent. Non-limiting examples of reducing agents include thiosulphates, iodides, dithionates, formates, and bisulfites. According to certain embodiments, the solvent comprises one or more basic solutions and an additive that is a reducing agent.

In some embodiments, the solvent is capable of near instantaneous dissolution of zirconium present in the coating of the metal substrate. In other embodiments, the solvent may take a period of time to dissolve the zirconium, and therefore the method may include a waiting period.

Once the zirconium has been converted to water-soluble form in a test solution formed with the solvent, an indicator may be added to the test solution, as indicated by step 245 in FIG. 2. In accordance with at least one embodiment, the indicator changes color in the presence of zirconium. Method 200 of FIG. 2 therefore includes step 250 for determining if a color change occurs in the test solution. As used herein, the term "indicator" when used in reference to zirconium, refers to a substance that will react or complex with a threshold level of zirconium to display a color change. In some instances, the threshold level may be as low as 0.0006%. In addition, the indicator must not react with any of the alloy elements present in the metal substrate. In accordance with some embodiments, the indicator may be morin hydrate or arsenazo I hydrate. For example, arsenazo I hydrate turns a dark blue-violet color, and morin hydrate turns an intense yellow fluorescent color, in the presence of zirconium. Other non-limiting examples of indicators include p-dimethylaminoazophenylarsenic acid (pararsonic acid), pyrocatechol violet, rufigallic acid, and xylenol orange.

The amount of indicator added to the test solution may be any amount sufficient to induce and allow for detection of a color change of the test solution if zirconium is present in the test solution. In some embodiments, the amount of indicator added to the test solution may depend on the solvent used. In accordance with some embodiments, the indicator may be added using a dropper, such as an eye dropper, or a pipette. According to one embodiment, several drops or one large drop of solvent may be added to the metal substrate and then one or more drops of the indicator may be added to the test solution created by the solvent and any dissolved zirconium species.

In accordance with some embodiments, the solvent and the indicator may be added to the metal substrate at the same time. For instance, the solvent and indicator may be mixed together and then applied to the surface of the metal substrate. Therefore, steps 235 and 245 of FIG. 2 may be performed in one step. In some embodiments, the solvent and indicator may be added in equal amounts. According to certain embodiments, the ratio of solvent to indicator may be between 5:1 and 1:1 by weight. The amount of indicator added or otherwise included with the solvent may be an amount needed to cause an observable color change but not an amount so excessive that it inhibits the reaction or otherwise inhibits an observable color change.

In some embodiments, the indicator may be in solid form, i.e., the indicator may be a paper having the indicator disposed on one or more surfaces. The paper may come into contact with the test solution, and the indicator may turn color based on the presence of zirconium. In other instances, the indicator may be a powder or gel. In some instances, the powder or gel can be added to the test solution, and in other instances, the powder or gel may be dissolved or mixed with a liquid solution first, and then added to the test solution.

According to some embodiments, the color change can be observed with the naked eye. In other embodiments, the color change can be observed by using an emission or absorption spectrophotometer. For instance, all or a portion of the test solution containing the indicator and any dissolved zirconium may be siphoned or otherwise removed from the metal substrate and introduced into a device, such as the emission or absorption spectrophotometer.

Method 2—Colorimetric Test with Fusion Flux

According to another embodiment, a fusion flux process (also referred to as a flux fusion process) may be used for determining the presence of trivalent chromium conversion coating. One example of this process is shown generally at 300 in the process flow diagram of FIG. 3. The flux material may be used to render zirconium in the metal conversion coating to a more water-soluble form. For instance, the zirconium of the mixed metal oxide that comprises the coating may be converted to a readily acid digestible material through use of a flux material. According to one embodiment, zirconium is converted to a form that readily reacts with hydrochloric acid to yield a water-soluble form of zirconium, e.g., zirconyl chloride. Other water-soluble forms of zirconium are also within the scope of this disclosure. For instance, nitrates, fluorides, chlorides, and other soluble zirconium salts formed from a corresponding acid may also be used in accordance with the processes described herein.

The process involves a first step 330 of contacting the surface of the metal substrate that has undergone a conversion coating process with a flux material. One example of a suitable flux material includes solid basic salts, and according to one embodiment, one or more solid basic salts may be used as the flux material. Non-limiting examples of solid basic salts include borates and carbonates of the alkali metals, such as sodium carbonate, lithium metaborate, lithium tetraborate, sodium tetraborate, lithium carbonate, and combinations thereof. According to some embodiments, the flux material may be a mixture of one or more solid basic salts. For instance, the flux material may be a 50:50 mixture of lithium metaborate and lithium tetraborate. The flux material may be any suitable material that renders the zirconium into a more soluble form.

The flux material may be provided in a powder form and may be applied as a layer onto the surface of the metal substrate. For instance, powdered flux material may be deposited onto the metal substrate as a continuous layer, or may be applied as a discontinuous layer, such that when heated (as described in further detail below) the deposited layer provides enough material to render the zirconium in the coating to a more soluble form for purposes of the test. A small amount of water may also be added to the powder flux material and mixed with the powder to form a paste to aid in applying the material to the surface of the metal substrate. In some instances, the layer of flux material may cover a few millimeters of the surface of the metal substrate. In other instances, the layer may cover a larger area. For instance, in some embodiments, the layer of flux material, and hence the test sample size, may be about the size of a coin.

Once the flux material is added to the metal substrate, the metal substrate is heated at step 332 to a predetermined temperature to fuse the flux material with the coating. The metal substrate may be heated to any temperature sufficient to effect thermal diffusion of the flux material, such as the base salt, into the coating and allow for the formation of a zirconium salt. According to some embodiments, the heat may be applied at a temperature in a range of from about 900° C. to about 1000° C. Heating may be performed for a period of time sufficient to effect thermal diffusion of the flux, but yet not harm the underlying metal substrate. In instances where the flux material is a solid basic salt, the basic salt may react with the zirconium using the same reaction mechanism discussed above in reference to the first part of Equation (2).

Heating may be performed in a furnace and therefore may require samples of the metal substrate to be of a size that is capable of being placed into the interior of the furnace. According to an alternative embodiment, spot heating may be performed using a heating probe configured to provide localized heat to the test area. For instance, the heating probe may include a heating element, such as a filament, that can be heated to the required temperature required to perform the fusion process. The heating element may be capable of heating to a temperature of about 1000° C. in a few microseconds. Using such a heating probe may allow for the metal substrate comprising the sample to be of any size, since only a small portion of the entire substrate needs to be tested. Other heat sources capable of functioning as an energy source are also within the scope of this disclosure, such as lasers. For instance, one or more diode lasers may be directed at the flux material disposed on the surface of the metal substrate for purposes of heating and initiating the flux process. Other heat application methods and devices are also within the scope of this disclosure, including spark plasma sintering devices.

Figure 3:
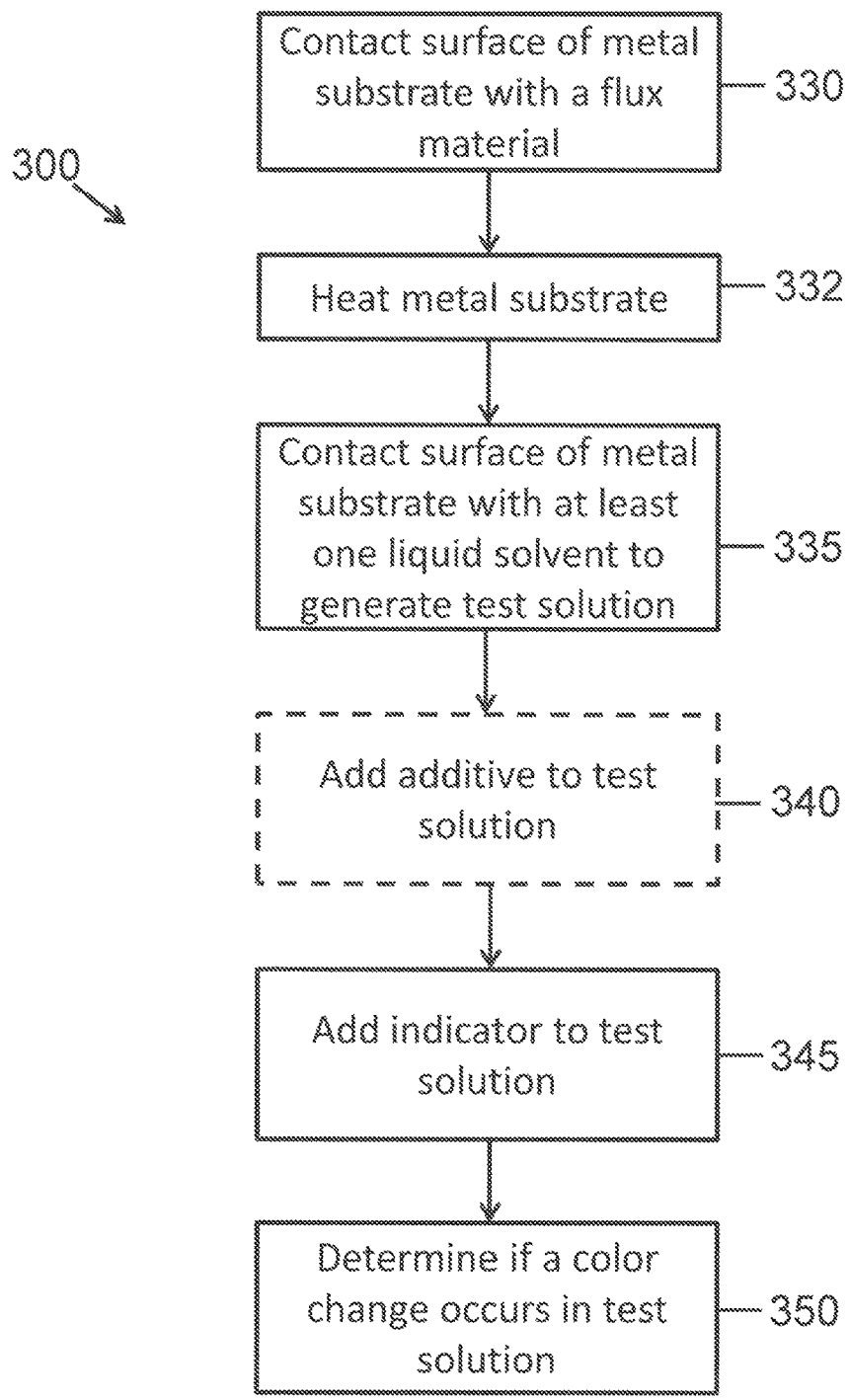
FIG. 3 is a functional block diagram illustrating one example of a colorimetric test method using fusion flux in accordance with one or more aspects of the present invention.

Once the zirconium is treated with the flux material and heated, the surface of the metal substrate may be contacted with one or more solvents, such as an acid, to form a test solution, as indicated in step 335 of FIG. 3. For instance, one or more acids may be added according to the second part of Equation (2) as discussed above to form a water-soluble form of zirconium. For example, in some embodiments, the acid may be hydrochloric acid, hydrofluoric acid, or nitric acid. In some instances, the one or more acids are capable of near-instantaneous conversion of zirconium into a water-soluble form, whereas in other instances step 335 may require a waiting period.

Once the zirconium has been rendered into a water-soluble form in a test solution formed with the one or more solvents, an indicator may be added to the test solution at step 345. The indicator may be added to the test solution as previously described and characterized in step 245 of FIG. 2. For instance, an amount of indicator, such as morin hydrate or arsenazo I hydrate, may be added to the test solution. The amount of indicator added is an amount sufficient to induce a color change of the test solution if zirconium is present in the test solution. Step 350 is similar to step 250 described above in reference to FIG. 2, and includes determining if a color change occurs in the test solution. As discussed above, the color change can be observed with the naked eye, or may be observed by using a device capable of determining a color changes, such as an emission or absorption spectrophotometer.

In some embodiments, the indicator may be introduced to the zirconium salt at the same time as the one or more solvents. For instance, a solvent, such as an acid, and the indicator may be mixed or otherwise provided as a mixture in an appropriate ratio, as described above. This implies that steps 335 and 345 may be performed in a single step.

Process 300 also optionally includes step 340, which includes the use of one or more additives and is similar to the discussion above in reference to step 240 of FIG. 2.

Method 3—Colorimetric Test with Electrolysis

Figure 4:
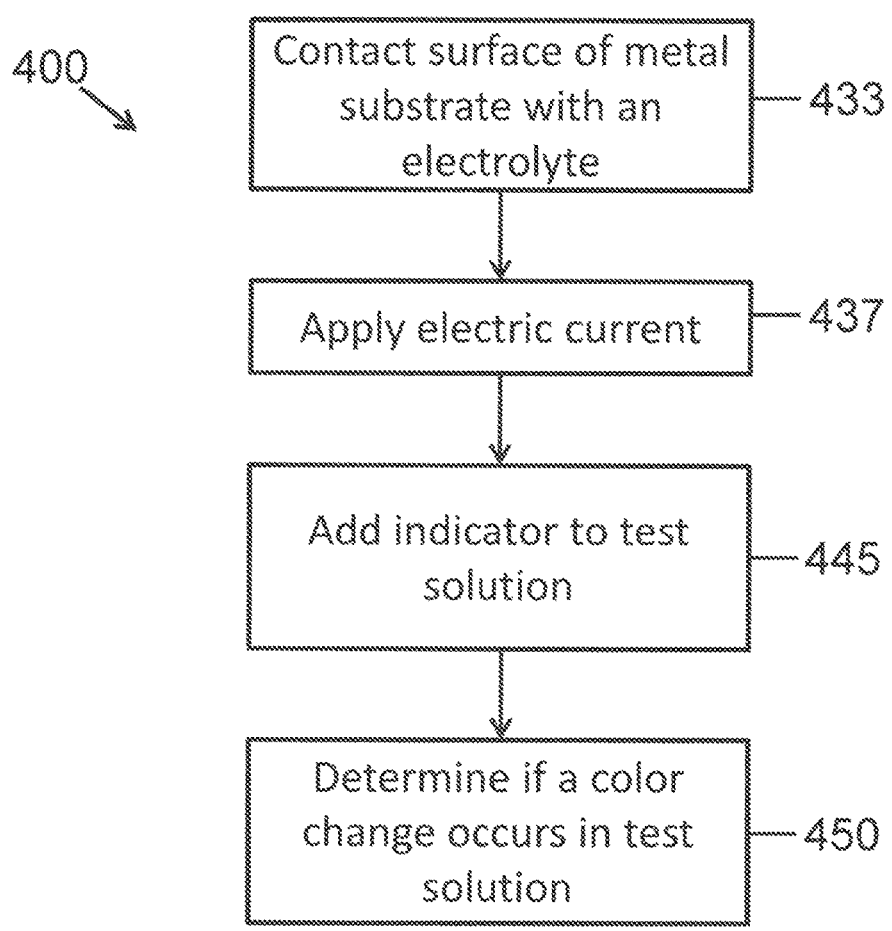
FIG. 4 is a functional block diagram illustrating one example of a colorimetric test method using electrolysis in accordance with one or more aspects of the present invention.

According to another embodiment, electrolysis may be used in a method for detecting the presence of a trivalent chromium conversion coating. A general process flow for this method is generally indicated at 400 in FIG. 4. In general, the term "electrolysis" refers to a method of using an electric current to initiate a chemical reaction. According to the methods discussed herein, electric current may be coupled with various electrolyte solutions to electrolytically and/or chemically generate zirconium ions in solution from trivalent chromium treated surfaces. For instance, an electric current may be passed through an aqueous solution comprising one or more electrolytes which converts the zirconium in the coating to a water-soluble form of zirconium. The reaction is shown below by Equation (3):

Equation (3):

where: A is the anion of the zirconium salt formed, and x and y are dependent on the electrolyte used. Process 400 begins at step 433 by contacting the surface of the metal substrate that has undergone a trivalent chromium conversion process with an electrolyte. In some embodiments, the electrolyte may be any one or more of the acids discussed above in reference to Equation (1). In certain instances, applying an electric current may enhance the ability to form a more water-soluble form of zirconium. In some embodiments, the electrolyte may be any one or more salt solutions, such as those formed from dissolved chlorides, fluorides, and nitrates. An electrolyte formed from a mixture of one or more acids and a salt solution may also be used. The metal substrate may be completely immersed in the electrolyte, or a portion of the metal substrate may be immersed in the electrolyte.

At step 437 an electric current is applied to the electrolyte. The electric current may be applied at a predetermined level and for a predetermined period of time sufficient to convert at least a portion of the zirconium present in the coating to a water-soluble form of zirconium. Once this has occurred, the electrolyte functions as a test solution, and an indicator may be added to the test solution at step 445. The indicator may be added at step 445 as previously described and characterized in step 245 of FIG. 2. For instance, an amount of indicator, such as morin hydrate or arsenazo I hydrate, may be added to the test solution. Step 450 includes determining if a color change occurs in the test solution generated by the electrolyte and any dissolved zirconium, and is similar to step 250 described above in reference to FIG. 2. A color change indicates the presence of zirconium and confirms the presence of a trivalent chromium conversion coating. In some embodiments, the indicator may be added to the electrolyte before applying the electric current at step 437.

Other Methods of Forming Soluble Zirconium

According to one embodiment, a water-soluble form of zirconium, such as zirconyl chloride, may be formed from contacting the surface of the metal substrate with a chlorinating reagent. One example of such a chlorinating reagent is phosphorus pentachloride. According to this example, phosphorus pentachloride ($PCl_5$) may be added as a layer onto the surface of the metal substrate. The surface may then be heated to a temperature of about 190° C., and the phosphorus pentachloride reacts with the zirconium oxide present in the conversion coating to generate zirconyl chloride. The zirconyl chloride may then be dissolved in a solution such as water or a dilute acid such as hydrochloric acid to form a test solution. An indicator may then be added to the test solution for purposes of detecting a color change and confirming the presence of a trivalent chromium conversion coating, as discussed above.

Kit for Performing Analysis

In accordance with at least one embodiment, a kit is provided for determining the presence of a trivalent chromium conversion coating on a metal substrate that has been subjected to a chromate conversion process. The kit may therefore contain one or more physical components that may be used to carry out the methods disclosed herein.

Figure 5A:
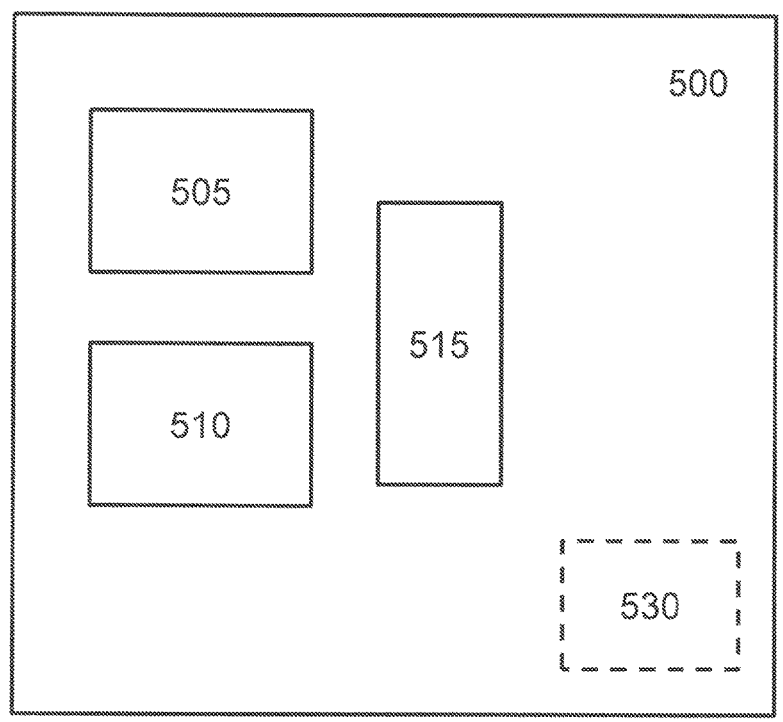
FIG. 5A is a block diagram of one example of a kit in accordance with one or more aspects of the present invention.

Referring to FIG. 5A, according to one embodiment, a kit 500 comprises a solvent 505, and an indicator 510 capable of detecting zirconium. The indicator 510 may be added to a test solution formed from contacting the solvent 505 with a surface of the metal substrate to induce a color change of the test solution if zirconium is present in the test solution. For instance, the solvent 505 may comprise one or more protic acids, as described above, such as hydrochloric, hydrofluoric, and/or nitric acid, and the indicator 510 may be morin hydrate or arsenazo I hydrate.

The solvent 505 and/or the indicator 510 may be provided in a container such as a bottle or vial and may include enough testing material to perform multiple tests. In some instances the bottle or vial may be opaque or colored so as to avoid degradation or other detrimental effects caused by light to the solvent or indicator. In instances where the solvent and indicator are mixed together to provide one liquid solution, a single container may be used.

In some embodiments, the kit 500 also comprises at least one dispensing device 515 for dispensing at least one of the solvent 505 and the indicator 510 onto a surface of the metal substrate. For instance, the at least one dispensing device 515 may be a pipette, a stick, a syringe, or an eye dropper that includes a squeeze bulb, for purposes of drawing the material and dispensing it onto the surface of the metal substrate. In some instances, the dispensing device 515 may be attached to the container that contains the solvent 505 and/or indicator 510. For instance, an eye dropper dispenser may be removably attached to the container. In other embodiments, the indicator 510 may be provided on a paper, or in another solid form, as described above.

Figure 5B:
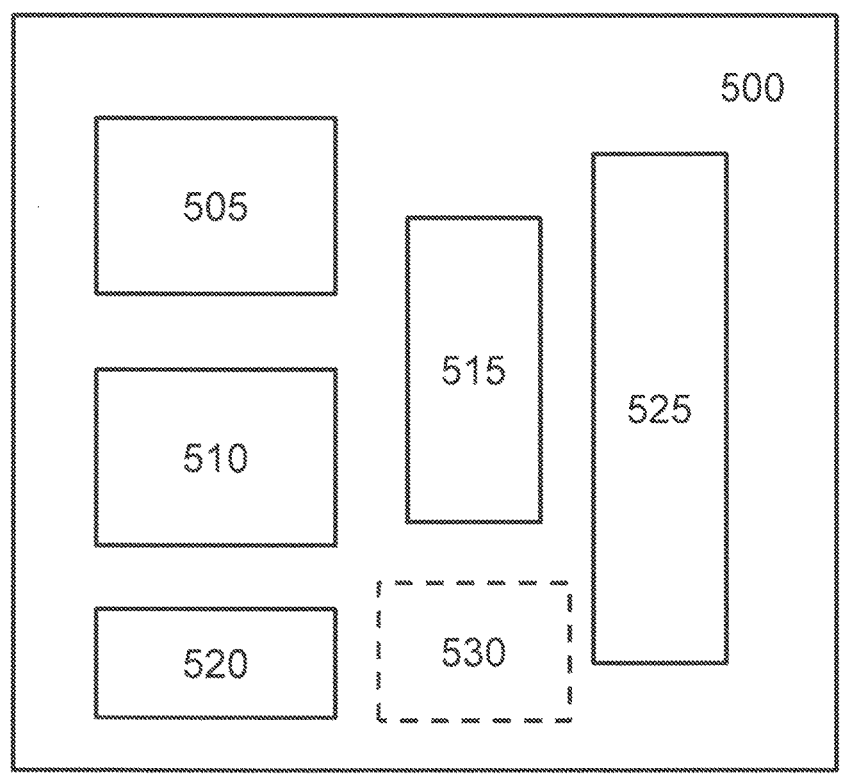
FIG. 5B is a block diagram of another example of a kit in accordance with one or more aspects of the present invention.

Referring to FIG. 5B, according to another embodiment, a kit 500 includes a solvent 505, an indicator 510, and at least one dispensing device 515, as described above. In addition, the kit 500 may also comprise a flux material 520. The flux material 520 may be any of the flux materials described herein. For instance, the flux material 520 may be a solid basic salt, such as a borate or a carbonate of an alkali metal. The flux material 520 may also be provided in a container and may also include a dispensing device, such as a spatula, spoon, or scoop, which may be used to add a layer of the flux material onto the surface of the metal substrate. In accordance with another embodiment, the kit 500 may also comprise a heating device 525. The heating device 525 may be used to heat the flux material disposed on the surface of the metal substrate to a predetermined temperature. The heating device 525 may be a heating device as described above, such as a heating probe or diode laser. For instance, the heating device 525 may be a heating probe that includes a filament or other heating element that is configured to heat the flux material to a temperature of about 1000° C. The heating device 525 may be configured to heat to any temperature sufficient to effect thermal diffusion of the flux material.

In some embodiments, the kit 500 may also include one or more additives 530, such as an oxidizing or reducing agent, and is indicated as an optional component of the kits shown in FIGS. 5A and 5B. One or more additives 530 may be included separately, i.e., in separate containers and dispensing devices, or may be included with other components of the kit. For instance, one or more oxidizing agents may be included with the solvent. In other instances, the oxidizing agent may be included in a separate container that may be configured to protect or otherwise inhibit the oxidizing agent from reacting with the air or other components, such as the solvent 505, thereby reducing their effectiveness.

The aspects disclosed herein in accordance with the present invention, are not limited in their application to the details of construction and the arrangement of components set forth in the following description or illustrated in the accompanying drawing. These aspects are capable of assuming other embodiments and of being practiced or of being carried out in various ways. Examples of specific implementations are provided herein for illustrative purposes only and are not intended to be limiting. In particular, acts, components, elements, and features discussed in connection with any one or more embodiments are not intended to be excluded from a similar role in any other embodiments.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated reference is supplementary to that of this document; for irreconcilable inconsistencies, the term usage in this document controls. Moreover, titles or subtitles may be used in the specification for the convenience of a reader, which shall have no influence on the scope of the present invention.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

What is claimed is:

1. A method of testing for the presence of a trivalent chromium conversion coating on a metal substrate that has been subjected to a chromate conversion process, comprising:
    contacting a surface of the metal substrate with at least one solvent to generate a test solution, the at least one solvent being capable of dissolving zirconium to produce a water-soluble form of zirconium;
    adding an indicator capable of detecting zirconium to the test solution in an amount that induces a color change of the test solution if zirconium is present in the test solution; and
    confirming the presence of the trivalent chromium conversion coating based on detecting the color change in the test solution.

2. The method of claim 1, wherein the at least one solvent comprises at least one protic acid.

3. The method of claim 1, wherein contacting the surface of the metal substrate comprises:
    contacting the surface of the metal substrate with at least one base; and
    contacting the surface of the metal substrate with at least one acid.

4. The method of claim 3, wherein the at least one base is a basic solution.

5. The method of claim 1, further comprising:
    contacting the surface of the metal substrate with a flux material; and
    heating the metal substrate to a predetermined temperature prior to contacting the surface of the metal substrate with the at least one solvent.

6. The method of claim 5, wherein the flux material is a solid basic salt.

7. The method of claim 6, wherein the solid basic salt is a borate or a carbonate of an alkali metal.

8. The method of claim 5, wherein the at least one solvent is a protic acid.

9. The method of claim 1, wherein the at least one solvent includes at least one additive.

10. The method of claim 9, wherein the at least one additive is one of an oxidizing agent and a reducing agent.

11. The method of claim 1, wherein the indicator does not chemically react with any alloys present in the metal substrate.

12. The method of claim 1, wherein the indicator is one of morin hydrate and arsenazo I hydrate.

13. A kit for determining the presence of a trivalent chromium conversion coating on a metal substrate that has been subjected to a chromate conversion process, comprising:

a solvent capable of dissolving zirconium to produce a water-soluble form of zirconium; and an indicator capable of detecting zirconium in a test solution formed from contacting the solvent with a surface of the metal substrate.

14. The kit of claim 13, wherein the solvent comprises at least one protic acid.

15. The kit of claim 14, wherein the at least one protic acid is one of hydrochloric acid, hydrofluoric acid, and nitric acid.

16. The kit of claim 13, further comprising a flux material.

17. The kit of claim 16, wherein the flux material is a borate or a carbonate of an alkali metal.

18. The kit of claim 13, wherein the indicator is one of morin hydrate and arsenazo I hydrate.

19. The kit of claim 13, wherein the solvent and the indicator are provided together in a single solution.

\* \* \* \* \*

UNITED STATES PATENT AND TRADEMARK OFFICE
CERTIFICATE OF CORRECTION

| | |
|---|---|
| PATENT NO. | : 10,274,468 B2 |
| APPLICATION NO. | : 15/353047 |
| DATED | : April 30, 2019 |
| INVENTOR(S) | : William J. Wolfgong et al. |

Page 1 of 1

It is certified that error appears in the above-identified patent and that said Letters Patent is hereby corrected as shown below:

In the Specification

Column 2, Line 54, delete "morn" and insert -- morin --.

Column 3, Line 4, delete "morn" and insert -- morin --.

Signed and Sealed this
Eighteenth Day of June, 2019

Andrei Iancu
*Director of the United States Patent and Trademark Office*